United States Patent [19]

Galbraith

[11] 4,378,159
[45] Mar. 29, 1983

[54] SCANNING CONTAMINANT AND DEFECT DETECTOR

[75] Inventor: Lee K. Galbraith, Mountain View, Calif.

[73] Assignee: Tencor Instruments, Mountain View, Calif.

[21] Appl. No.: 249,226

[22] Filed: Mar. 30, 1981

[51] Int. Cl.³ ............................................. G01N 21/00
[52] U.S. Cl. ..................................... 356/237; 356/236
[58] Field of Search .............. 356/236, 237, 430, 431, 356/446; 250/562, 563, 571, 572

[56] References Cited

U.S. PATENT DOCUMENTS

| 3,790,287 | 2/1974 | Cuthbert | 356/120 |
| 3,931,525 | 1/1976 | Clarke | 356/430 X |
| 4,321,630 | 3/1982 | Kramer | 250/228 X |

OTHER PUBLICATIONS

"A Laser Scan Technique for Electronic Materials Surface Evaluation," Oswald and Munro (Bell Laboratories) in *Journal of Electronic Materials*, vol. 3, No. 1, p. 225 (1974).
"Optical Scanning of Silicon Wafers for Surface Contaminants," Martin and Williams in *Electro-optical Systems Design*, p. 45, Sep. 1980.
Drawing from Coptec, Inc. SemiScan 3 advertisement.
Block diagram from Ford Aerospace & Communications Corporation, "Automatic Laser Fabric Inspection and Control Systems" brochure.

*Primary Examiner*—John K. Corbin
*Assistant Examiner*—Matthew W. Koren
*Attorney, Agent, or Firm*—Thomas Schneck

[57] ABSTRACT

A scanning laser contaminant and defect detector for reflective surfaces, having a light collector for increasing sensitivity to scattered light. The collector is preferably one quadrant of a spherical shell cradled between V-shaped reflective side walls. The collector has beam entrance and exit ports, as well as a detector port where a light detector resides. The collector is placed in proximity to a surface to be inspected. Light scattered from the test surface is directed to the reflective crown surface, then to the reflective side walls and ultimately to the detector.

12 Claims, 3 Drawing Figures

SCANNING CONTAMINANT AND DEFECT DETECTOR

DESCRIPTION

1. Technical Field

The invention relates to optical flaw or contaminant detectors and more particularly to a scanning laser contaminant detector for reflective surfaces, such as silicon wafers.

2. Background Art

In U.S. Pat. No. 3,790,287 J. Cuthbert, et al. describe a scanning laser contaminant detector which relies upon diminution in the intensity of a retroreflected beam when a defect or contaminant is encountered by the beam. Cuthbert recognized that it is more advantageous to detect defects by means of scattered light rather than by diminishment of the intensity of the specularly reflected return beam. Cuthbert utilized a spatial filter to intercept the retroreflected beam and segregate scattered light surrounding the beam. The scattered light was transmitted to a detector for measuring contaminants.

Hemispherical integrating light collectors are known. These collectors have a light entrance port and a detector port angularly spaced relative to the entrance port. Such integrating collectors are used to gather light diffusely reflected or scattered from an object below the beam entrance port.

In an article entitled "Optical Scanning of Silicon Wafers for Surface Contaminants" in Electro-Optical Systems Design, September, 1980, p. 45-49 M. Martin, et al. disclose a wafer scanning apparatus in which a detector is set at an acute angle relative to a beam from a source. The specularly reflected beam is avoided and only angularly scattered radiation is viewed. The detector of Martin, et al. attempts to achieve an improved signal-to-noise ratio by avoiding the specular retroreflected beam with an angular spacing of the detector.

In summary, the prior art teaches that scanning laser flaw and contaminant detectors are known. The prior art recognizes that flaws and contaminants yield an increase in light scattered from a scanning beam incident on an object to be inspected and that scattered light may be observed at an angle relative to an incident beam. It is also known that integrating light collectors may be used for light collection from a scattering surface.

One of the problems which is experienced in the prior art is that in measuring minor contaminants, the signal from scattering is so weak that background illumination may interfere with the scattering signal to be detected. The present invention seeks to reduce the impact of background radiation and provides a very sensitive flaw and contaminant detection system.

DISCLOSURE OF INVENTION

The above object has been achieved by providing a special light collector over a test surface. The collector is opaque on its outer surface, but reflective on its inner surface. The collector has a beam entrance port and a beam exit port directly beneath it. A detector port is located at an acute angle with the beam entrance port relative to a surface directly below the beam exit port. The light collector is a sector of a sphere supported on V-shaped plane mirrors with a slit, the beam exit port, defined between the mirrors. The collector internally directs light toward the detector port where a detector is mounted. Scattered light impinging on a detector mounted in the detector port, exceeding a predetermined threshold, is recorded and indicates the presence of a contaminant exceeding a threshold level. The collector behaves like a hemispherical integrating light collector, but has a more compact and functional construction. A surface placed beneath the exit port of the detector is scanned by light passing through a slit in the collector as a conveyor moves the surface along. The beam passing through the collector scans in a direction transverse to surface travel so that the combination of beam scanning and surface travel provides a two-dimensional sweep of the surface for defects.

BEST MODE FOR CARRYING OUT THE INVENTION

Figure 1:
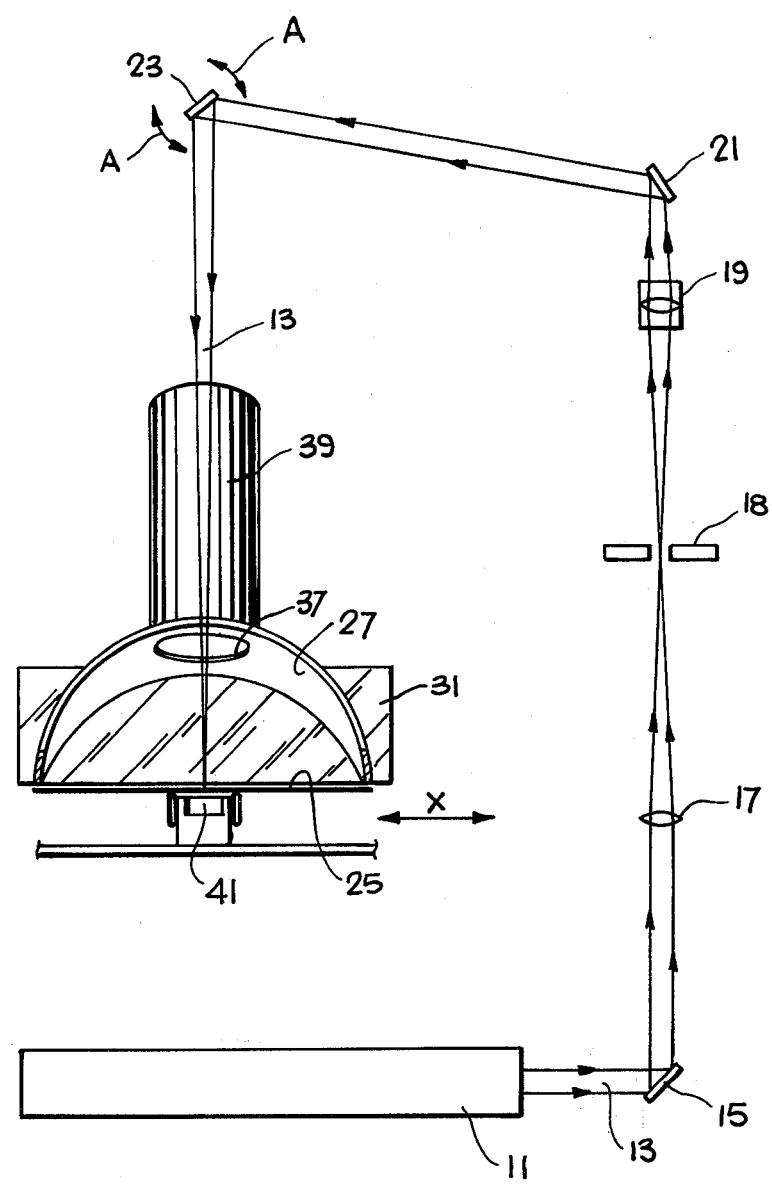
FIG. 1 is a simplified plan view of the optical contaminant detector of the present invention.

With reference to FIG. 1, a low power laser 11 may be seen directing a beam 13 toward mirror 15. Laser 11 can be a helium-neon general purpose laser having an output power of a few milliwatts. A higher power laser may be preferable for greater detection capability. In some instances blue light, e.g. from a helium-cadmium laser is preferred for detection of smaller defects than with a helium-neon laser. Beam 13 is directed to focusing lens 17 and then to a beam collimating and focussing lens 19. A spacial filter 18 a short distance from lens 17 allows only the central portion of the beam to proceed. The focal length of lens 19 is approximately 14 cm. From lens 19, the beam is directed toward fixed mirror 21 and then to galvanometer mirror 23. Galvonometer mirror 23 directs light so that the focal point of the beam is at the surface of the surface 25. The focal length of focussing optics 19 is long enough so that the beam stays in focus as it is swept across the surface 25, even though the beam makes a slightly arc-shaped trajectory. There is sufficient depth of field at this long focal length that a fine beam spot is maintained as the beam sweeps across the surface being scanned for defects.

The defect need not be highly reflective. Reflectivity above 7 to 10% is sufficient to be detected with a low power, helium neon laser with a sensitive detector, such as a photomultiplier tube, and the light collector of the present invention.

The light collector 27 is a sector, preferably a quadrant, of a spherical shell. The shell has a reflective coating, such as white paint, on the inside surface, facing surface 25, and an absorptive coating, such as black paint, on the outside surface. For purposes of illustration, only one-half of the shell is shown in FIG. 1. That half is shown resting on mirror surface 31 which forms half of a V-shaped trough in which the shell 27 rests. Shell 27 has a slit through which beam 13 enters. This slit is not visible in FIG. 1. The beam passes through an exit aperture 35, visible in FIG. 2, which is opposite the beam entrance aperture.

The upper portion of the shell is termed a "crown". The inner crown surface directs light toward the mirrors, then back to the crown, and so on, until light enters the detector. Note that the shell is positioned in proximity to the surface 25 with the crown distal to the test surface and the bottom of the V-shaped trough formed by the mirror side walls in close proximity to the test surface. This is done in order that a gap between the V-shaped walls, which forms the beam exit port, be very close to the test surface. Moreover, close proximity, within a few millimeters, allows most of the scattered light from the test surface to reenter the light collector. Specularly reflected light doubles back on the beam path toward the galvanometer mirror and is lost. On the other hand, light scattered at an angle to the incident beam is collected for measurement by the detector.

The V-shaped mirror side walls have two distinct functions. First, the walls serve to optically fold the sector, allowing for a compact collector. Second, the linear gap between the base of the side walls serves as a beam exit port for a scanning beam along a linear scanning path. Each of the side walls is inclined to the vertical by an angle of 45 degrees.

A detector port 37 is defined in the shell at an acute angle with the beam entrance port relative to test surface 25. A light detector, such as a silicon cell or preferably a photomultiplier tube 39 is mounted directly over the director detector port, in a light-tight relationship therewith.

The galvanometer mirror 23 moves back and forth at a high rate, such as 800 Hz, in directions indicated by the arrows A. This causes the beam to move back and forth across test surface 25 in the X direction. Independently of this motion, surface 25 is advanced in the Z direction by a transport 41 on which the test surface is carried.

Figure 2:
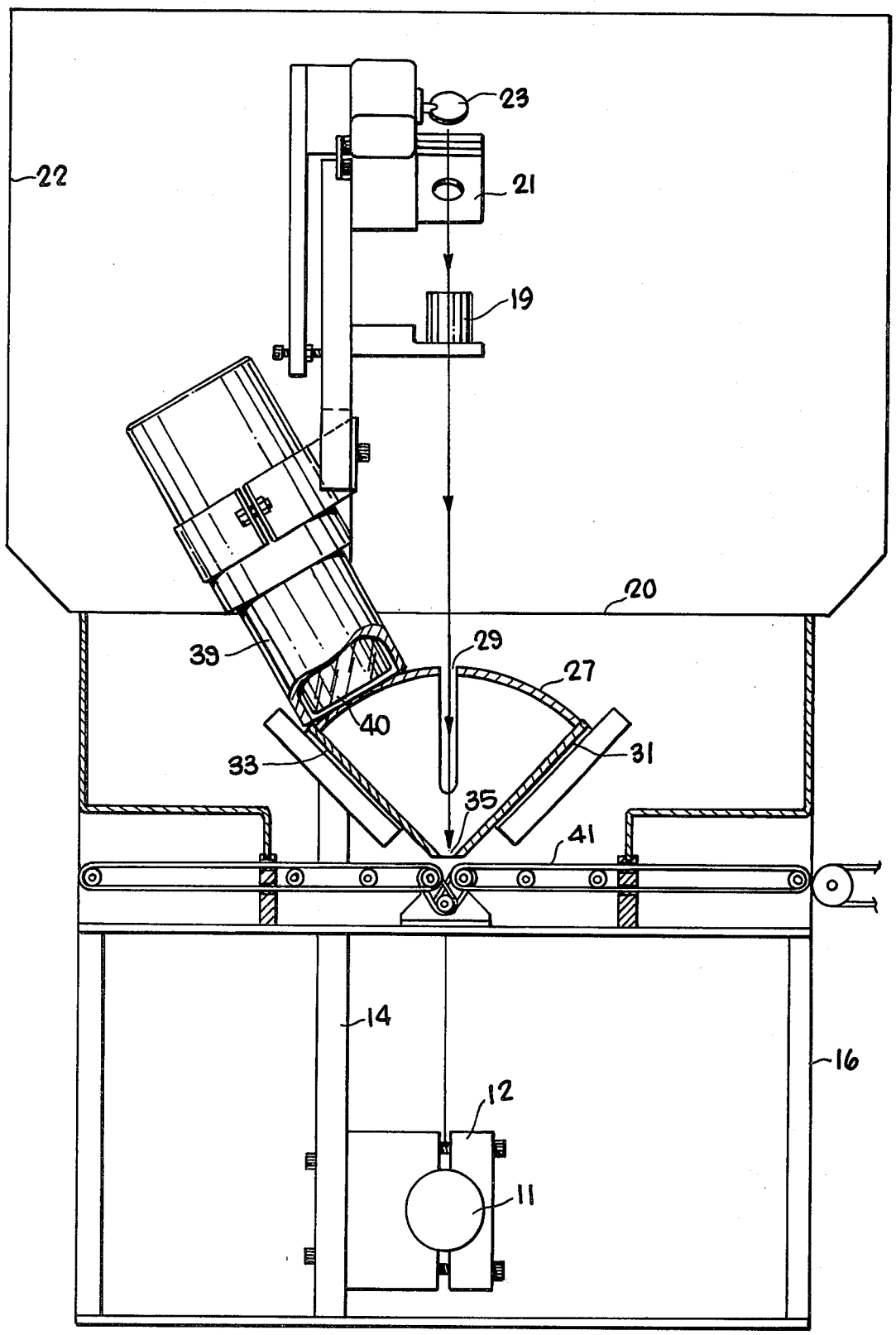
FIG. 2 is a side view of an optical contaminant detector instrument of the present invention in a partial housing.
Figure 3:
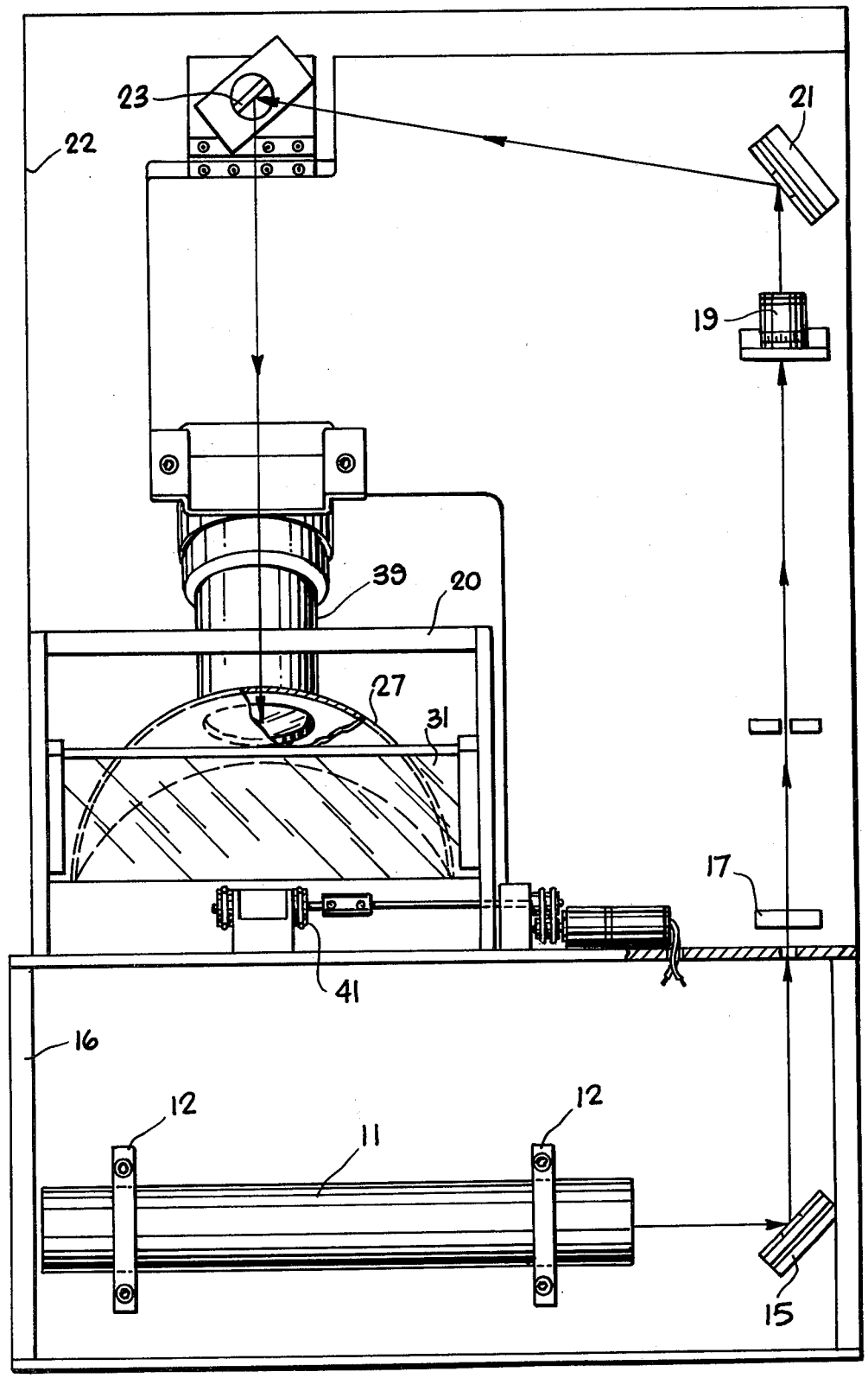
FIG. 3 is a front view of the instrument illustrated in FIG. 2.

FIGS. 2 and 3 show the apparatus of FIG. 1 in a partial housing formed by lower compartment 16 and upper compartment 20. An opaque shroud, 22, completely covers the top of the apparatus above the upper compartment, providing a light tight shield, totally eliminating background illumination and providing safety.

With reference to FIGS. 2 and 3, the lower power laser 11 may be seen to be mounted in a holder 12 which is bolted to a wall 14 in a lower compartment 16. Light from the laser is directed upward from mirror 15 and lens 17 through the focussing lens 19, mirror 21 and galvanometer mirror 23, thence downward through an opening 18 in upper compartment 20. The upper compartment provides a support for reflective article transport 41, as well as for the light collector. The light collector comprises the V-shaped flat mirrors 31 and 33, as well as the sector shell 27. An entrance aperture 29 may be seen to be immediately above an exit aperture 35 which is in a gap between the V-shaped mirror members 31 and 33.

Detector 39 may be seen making an acute angle with entrance aperture 29 relative to exit aperture 35. A test article, moving along conveyor 41 will pass immediately beneath the exit aperture 35. Any defects on the test surface or contaminants thereon will cause scattering of the beam. Upwardly scattered light will be scattered toward the reflective upper surface of shell 27 whereupon the light will be reflected to one of the mirrors 31 or 33. Eventually, light will enter the window 40 of detector 39. Preferably, detector 39 is a red-sensitive photomultiplier tube in the instance where laser 11 is a helium neon laser.

The output of the photomultiplier tube 39 is connected to a comparator, which also receives an input from a variable reference. The variable reference is a signal corresponding to the amount of scattering detected from a particle having a predetermined size which may be, for example, one square micron. Any detector signal which is above the reference level causes the comparator to produce an output signal.

As previously mentioned, the transport 41 moves a surface to be tested, such as a semiconductor wafer, past the beam exit port 35. The surface slowly moves transverse to the X-direction sweep by the beam at a known rate. Beam position is known because the position of the galvanometer mirror 23 is known. The galvanometer mirror provides an X-direction address for the beam. Similarly, motion of the transport motor provides an independent Z-direction address.

The addresses are used in a random access memory to provide addresses for scattering intensities which are observed by the detector. Three-by-three memory cells are observed using the known technique of cluster analysis. Briefly, columns of the three-by-three array cells are analyzed one at a time, left to right. The arrays are searched for aligned memory cells containing scattering data. For example, three cells in a row, each containing scattering data, would indicate the presence of a line defect. On the other hand, a single isolated memory cell containing a reading would indicate the presence of a particle. Two or three non-aligned cells containing detector data would similarly indicate one or more particles, rather than a line. The complete random access memory array of several thousand cells is analyzed in this way. At the same time, the memory array may be used to refresh a CRT or similar display device.

Light from a contaminant on a scanned surface is scattered upwardly at an angle with respect to the downwardly directed beam. Upwardly scattered light is collected at the detector with an efficiency of approximately 30%. The detector signal is independent of the scattering angle from 0 degrees to 45 degrees measured with reference to the vertical angle made by the entrance beam. The detector signal is also independent of the position of a defect or contaminant along a scanned line.

The light collector of the present invention is referred to as "internally reflecting". By the term "internally reflecting" is meant that an attempt is made to capture light scattered or diffusely reflected into the collector. Within the collector, light is specularly reflected from the V-shaped mirror side walls and diffusely reflected or scattered from the curved sector wall until captured at the detector or lost. The present light collector is not internally reflecting in the same manner as a fiber optic fiber, which relies on differences in the index of refraction between a medium in which light is traveling and a surrounding medium. This light collector provides a very sensitive angle and position independent flaw detection device for a scanning beam inspecting a surface for flaws and contaminants.

I claim:
1. Apparatus for detecting contaminants and defects on a reflective test surface comprising,
a light source capable of generating a narrow beam,
optical means for directing the beam toward a test surface to be inspected,
a support holding the surface,
scanning means for sweeping the beam in a path across the test surface, a light collector disposed over the test surface and having a beam entrance port, means for directing the beam onto the test surface and a detector port spaced apart from the beam entrance port, said collector comprising a sector of an internally diffusely reflecting spherical shell, said shell cradled between specularly reflective, flat converging side walls, said shell having a crown region, and light detection means mounted in the detector port for detecting increases in light scattering gathered by the light collector.

2. Apparatus for detecting contaminants and defects on a reflective test surface comprising, a light source capable of generating a narrow beam, optical means for directing the beam toward a test surface to be inspected, a support holding the surface, scanning means for sweeping the beam in a path across the test surface, a light collector disposed over the test surface and having a beam entrance port, a beam exit port over the test surface and a detector port making an acute angle with the beam entrance port relative to the test surface, said collector comprising a sector of an internally diffusely reflecting spherical shell, said shell cradled between specularly reflective, flat converging side walls, said shell having a crown region wherein said beam entrance port is defined, the beam exit port being defined in a gap between the converging side walls with the beam exit port optically aligned with the beam entrance port along the beam path, and light detection means mounted in the detector port for detecting increases in light scattering gathered by the light collector.

3. The apparatus of claim 2 wherein said side walls are V-shaped.

4. The apparatus of claim 3 wherein said V-shaped side walls are flat mirrors.

5. The apparatus of claim 2 wherein said support is a wafer conveyor belt.

6. The apparatus of claim 2 wherein the side of said shell facing said side walls has a reflective coating.

7. Apparatus for detecting contaminants and defects on a reflective test surface comprising, a lower compartment housing a laser beam source, said lower compartment having a roof supporting an article conveyor belt for test surfaces, and an upper compartment directly over the lower compartment, the upper compartment communicating with the lower compartment through a passage for receiving the laser beam, the upper compartment having:

(i) optical means for directing the beam to be normally incident to a reflective test surface on the article conveyor belt, (ii) scanning means for sweeping the beam in a path across the test surface, (iii) an internally reflecting light collector disposed over the test surface, the light collector comprising a sector of an internally reflecting spherical shell, said shell cradled between reflective, flat converging side walls, said shell having a crown region defining a beam entrance port and a detector port making an acute angle with the beam entrance port relative to the test surface, the converging side walls of the shell having a linear gap at their region of convergence defining a beam exit port optically aligned with the beam entrance port along the beam path, and (iv) light detection means mounted in the detector port at an acute angle relative to the beam for detecting increases in light scattering from the test surface, whereby the article conveyor advances a test surface as the beam sweeps across the test surface so that dirt on test surface will scatter light toward said light detection means.

8. The apparatus of claim 7 wherein said side walls are V-shaped.

9. The apparatus of claim 8 wherein said V-shaped side walls are flat mirrors.

10. The apparatus of claim 7 wherein said support is a wafer conveyor belt.

11. The apparatus of claim 7 wherein the side of said shell facing said side walls has a diffusely reflective coating.

12. The apparatus of claim 7 wherein said laser beam source is mounted transversely in said lower compartment.

* * * * *